(12) United States Patent
Ken et al.

(10) Patent No.: US 6,984,240 B1
(45) Date of Patent: Jan. 10, 2006

(54) DETACHABLE MULTIDIAMETER VASOOCCLUSIVE COIL

(75) Inventors: Christopher G. M. Ken, San Mateo, CA (US); Abhijit Acharya, Saratoga, CA (US)

(73) Assignee: Target Therapeutics, Inc., Fremont, CA (US)

( * ) Notice: Subject to any disclaimer, the term of this patent is extended or adjusted under 35 U.S.C. 154(b) by 978 days.

(21) Appl. No.: 08/736,896

(22) Filed: Oct. 25, 1996

(51) Int. Cl.
*A61M 29/00* (2006.01)

(52) U.S. Cl. ...................................................... 606/200
(58) Field of Classification Search ................ 606/191, 606/195, 198, 200, 159, 127–128, 151, 108; 623/1, 12; 128/899
See application file for complete search history.

(56) References Cited

U.S. PATENT DOCUMENTS

| | | |
|---|---|---|
| 4,994,069 A | 2/1991 | Ritchart et al. |
| 5,234,437 A | 8/1993 | Sepetka |
| 5,250,071 A | 10/1993 | Palermo |
| 5,261,916 A | 11/1993 | Engelson |
| 5,304,194 A | 4/1994 | Chee et al. |
| 5,304,195 A | 4/1994 | Twyford, Jr. et al. |
| 5,312,415 A | 5/1994 | Palermo |
| 5,350,397 A | 9/1994 | Palermo et al. |
| 5,382,259 A | 1/1995 | Phelps et al. |
| 5,413,586 A | 5/1995 | Dibie et al. |
| 5,476,472 A | 12/1995 | Dormandy, Jr. et al. |
| 5,531,788 A * | 7/1996 | Dibie et al. ................ 606/200 |
| 5,639,277 A * | 6/1997 | Mariant et al. ............ 606/200 |
| 5,649,949 A * | 7/1997 | Wallace et al. ............ 606/191 |
| 5,891,058 A | 4/1999 | Taki et al. |
| 5,895,398 A * | 4/1999 | Wensel et al. ............ 606/159 |
| 5,919,187 A | 7/1999 | Guglielmi et al. |
| 5,925,062 A | 7/1999 | Purdy |
| 5,980,154 A * | 11/1999 | Record ........................ 404/97 |

FOREIGN PATENT DOCUMENTS

| | | |
|---|---|---|
| DE | 3203410 A1 | 2/1982 |
| DE | 3203410 | * 11/1982 |
| EP | 0734697 | 10/1996 |
| EP | 0747014 | 12/1996 |
| WO | WO 92/14408 | 9/1992 |
| WO | WO 92/21400 | 12/1992 |
| WO | WO 97/48351 | 12/1997 |
| WO | WO 98/02100 | 1/1998 |

\* cited by examiner

*Primary Examiner*—Vy Q. Bui
(74) *Attorney, Agent, or Firm*—Bingham McCutchen LLP

(57) ABSTRACT

A vasoocclusive helical coil having a proximal end that carries a coupling member for attaching the coil to the distal end of a wire and a proximal winding that has a smaller diameter than adjacent windings whereby the proximal end of the coil is positioned radially inwardly of the main body of the coil.

20 Claims, 1 Drawing Sheet

DETACHABLE MULTIDIAMETER VASOOCCLUSIVE COIL

TECHNICAL FIELD

This invention is in the field of vasoocclusion devices. More particularly it relates to a helical vasoocclusion coil one end of which is adapted to be detachably connected to a wire and in which the helix winding at that end has a smaller diameter than the adjacent windings.

BACKGROUND

Vasoocclusion devices are surgical instruments that are placed within vessels, typically via a catheter, to block the vessel or to fill a vascular cavity such as an aneurysm. One type of vasoocclusion device is in the form of a helical wire coil. See U.S. Pat. No. 4,994,069. The coil may be placed at the desired site in several ways. One involves loading the coil into the lumen of a catheter whose distal end is located at the site. The coil is then advanced through the catheter lumen using a pusher and expelled from the distal end of the catheter. Another involves detachably coupling the coil to the distal end of a wire, advancing the assembly to the site using a catheter, and uncoupling the coil from the wire at the site. U.S. Pat. Nos. 5,234,437; 5,250,071; 5,261,916; 5,304,195; 5,312,415; and 5,350,397 describe coils that are detachably coupled to a wire.

Detachable coils carry a member on their proximal end that detachably engages or interlocks with a member on the distal end of the wire. A problem experienced with such coils is that the member carried on the coil is oriented tangentially to the helical diameter of the coil. As such, when the coil is decoupled, the member extends tangentially outwardly from the helix diameter and may engage the vessel wall. (See FIG. 1 of the drawings) Such engagement may injure or even perforate the vessel wall.

A principal object of this invention is to provide a detachable helical vasoocclusive coil in which the member that attaches to the wire is not oriented tangentially to the diameter of the coil. Accordingly, the coils of this invention are less likely to injure the vessel wall.

DISCLOSURE OF THE INVENTION

One aspect of the invention is a helical vasoocclusion coil for use with a wire having a distal end, said coil having: (a) a proximal end adapted to detachably couple to the distal end of the wire; (b) a distal end; (c) a first diameter intermediate (a) and (b); and (d) a second diameter smaller than said first diameter at said proximal end whereby said proximal end is positioned radially inwardly of said first diameter.

Another object of the invention is an assembly for use in occluding a vessel or a cavity within a vessel comprising: a wire having a distal end that carries a first coupling member; and a helical vasoocclusion coil having: (i) a proximal end that carries a second coupling member that is detachably coupled to the first coupling member; (ii) a distal end; (iii) a first diameter intermediate (i) and (ii); and (iv) a second diameter smaller than said first diameter at said proximal end whereby the first coupling member is positioned radially inwardly of said first diameter.

MODES FOR CARRYING OUT THE INVENTION

Figure 2:
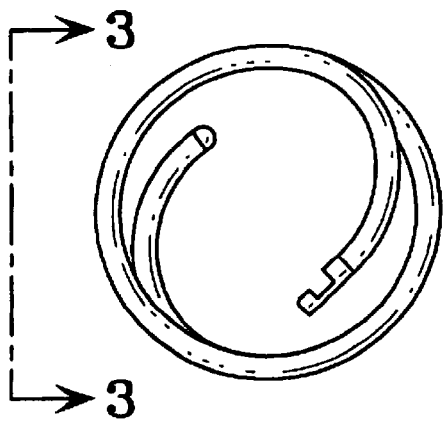
FIG. 2 is an elevational end view of one embodiment of the invention.
Figure 3:
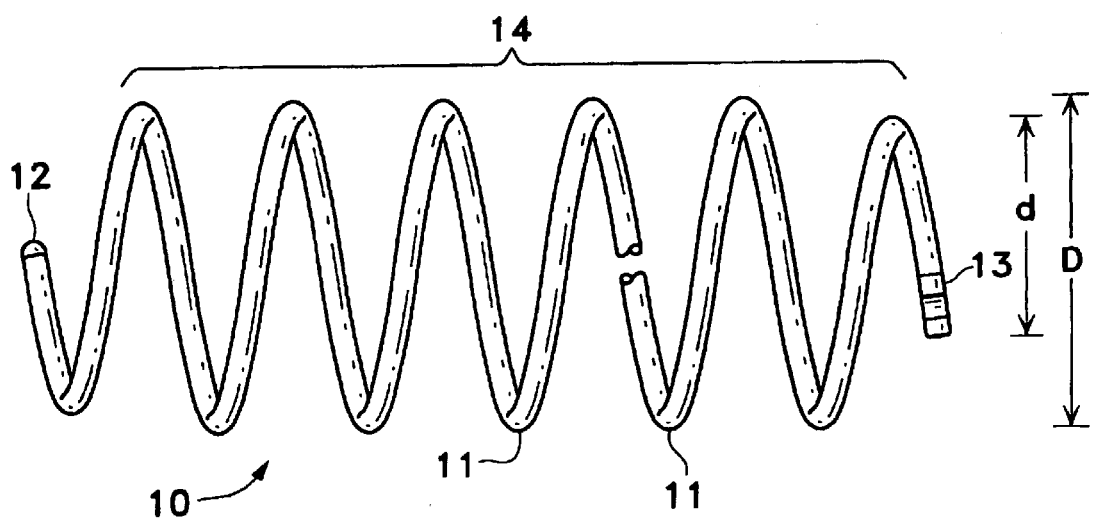
FIG. 3 is an elevational partial side view of the coil of FIG. 2.

FIGS. 2 and 3 depict an embodiment, generally designated 10, of the invention coil. Embodiment 10 is shown in its relaxed, helical configuration. As described in the art discussed in the Background section above, helical vasoocclusive coils are typically made of materials that have shape memories and can be deformed into an expanded, essentially linear shape for loading and advancement through a catheter to the site to be occluded. Once they are deployed from the catheter they assume a relaxed helical configuration, such as shown in FIG. 3.

Coil 10 is composed of a multiplicity of windings 11 and has a distal end 12 and a proximal end 13. The windings of coil 10 will typically be made of a metal such as platinum, gold, rhodium, rhenium, palladium, tungsten and the like or alloys of such metals. These metals have significant radiopacity and their alloys may be tailored to provide desired degrees of stiffness and flexibility. The windings may be made of other suitable biocompatible materials such as polymers or composites of metals and polymers.

While the cross-section of the windings of the coil 10 is circular, windings having other cross-sectional shapes, e.g. elliptical, trapezoidal, rhombic, rectangular, and square, may be used. Circular cross-sectional windings will typically have a diameter of about 0.01 to about 0.50 mm. Correspondingly, the diameter of the helix, D (FIG. 3), formed by the windings will normally be in the range of about 0.2 mm to about 30 mm. For neurovascular use the diameter of the helix will typically be in the range of 2.0 to 20 mm. The pitch of the windings may be uniform, as shown in FIG. 3, or may vary over a portion or the entire length of the coil. The axial length of the coil will usually be in the range of 0.5 to 100 cm, more usually 2 to 40 cm. The coil will usually have 10 to 75 windings per cm, more usually 10 to 40 windings per cm. It will be appreciated that the above-described dimensions are not critical and that dimensions that are suitable for occluding vascular sites within the human body are intended.

Figure 1:
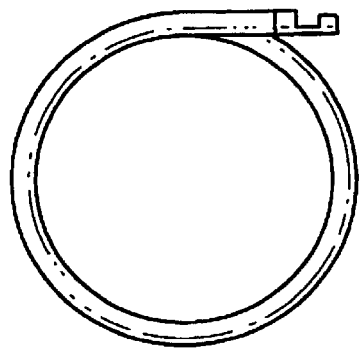
FIG. 1 is an elevational view of a prior art coil.

As shown in FIG. 3, the windings of the main body 14 of the coil form a helix of diameter D, whereas the proximal-most and distal-most windings have a diameter d that is smaller than D. As a result, the proximal and distal ends 12, 13, respectively, of the coil are located radially inwardly of the helix of main body 14 (FIG. 2) rather than being located tangentially to that helix (FIG. 1). Such positioning of the ends make the ends less likely to injure the vessel wall. As seen in FIGS. 2 and 3, the proximal end 13 of the coil has a slotted member 15 that is adapted to detachably couple to a mating member on the distal end of an elongated wire (not shown). Alternative mechanical coupling members are shown in U.S. Pat. Nos. 5,234,437; 5,250,071; 5,261,916; 5,304,195; 5,312,415 and 5,350,397, the disclosures of which with respect thereto are incorporated herein by reference.

While not shown in the drawings, the coil may have fibers attached to it to facilitate embolization. See U.S. Pat. Nos. 5,304,194; 5,476,472 and 5,382,259, the relevant disclosures of which are incorporated herein by reference. Other modifications of the above described modes for carrying out the invention that are considered obvious or equivalent by those of skill in the medical device art and related arts are intended to be within the scope of the following claims.

What is claimed is:

1. A vasoocclusion coil for use with a wire having a distal end, said coil having:
   a proximal end;
   a coupling member disposed on said proximal end and configured to detachably couple said proximal end to the distal end of the wire;
   a distal end;
   a coiled body formed of a multiplicity of windings having a proximal-most winding, a distal-most winding, and main body windings between said proximal-most and distal-most windings, said main body windings having a uniform first diameter, and said proximal-most and distal-most winding a second diameter smaller than said first diameter, wherein said proximal end and said distal end are positioned radially inwardly of said proximal-most and distal-most windings, respectively, and said coiled body acts to occlude a vessel or a cavity when placed within the vessel or cavity; and
   fibers attached to said windings for facilitating embolization.

2. The coil of claim 1 wherein said coupling member is configured to detachably interlock with the distal end of the wire.

3. The coil of claim 1, wherein said coil is a helical vasoocclusion coil.

4. The coil of claim 1, wherein said first diameter is in the range of 0.2 mm to 30 mm.

5. The coil of claim 1, wherein said first diameter is in the range of 2.0 to 20 mm.

6. An assembly for use in occluding a vessel or a cavity within a vessel comprising:
   an elongated wire having a distal end that carries a first coupling member; and
   a vasoocclusion coil having:
      a proximal end;
      a second coupling member disposed on said proximal end and detachably coupled to said first coupling member;
      a distal end;
   a coiled body formed of a multiplicity of windings having a proximal-most winding, a distal-most winding, and main body windings between said proximal-most and distal-most windings, said main body windings having a uniform first diameter, and said proximal-most and distal-most winding a second diameter smaller than said first diameter, wherein said proximal end and said distal end are positioned radially inwardly of said proximal-most and distal-most windings, respectively, and said coil acts to occlude a vessel or a cavity when placed within the vessel or cavity; and
      fibers attached to said windings for facilitating embolization.

7. The assembly of claim 6, wherein said second coupling member detachably interlocks with said first coupling member.

8. The assembly of claim 6, wherein said coil is a helical vasoocclusion coil.

9. The assembly of claim 6, wherein said first diameter is in the range of 0.2 mm to 30 mm.

10. The assembly of claim 6, wherein said first diameter is in the range of 2.0 mm to 20 mm.

11. A vasoocclusion coil, comprising:
    a proximal end;
    a distal end;
    a coiled body formed of a multiplicity of windings having a proximal-most winding, a distal-most winding, and main body windings between said proximal-most and distal-most windings, said main body windings having at least one winding having a first diameter, and said proximal-most and distal-most winding a second diameter smaller than said first diameter, wherein said proximal end and said distal end are positioned radially inwardly of said proximal-most and distal-most windings, respectively, and said coiled body acts to occlude a vessel or a cavity when placed within the vessel or cavity; and
    fibers attached to said windings for facilitating embolization.

12. The coil of claim 11, wherein said coil is a helical vasoocclusion coil.

13. The coil of claim 11, wherein said wherein said first diameter is in the range of 0.2 mm to 30 mm.

14. The coil of claim 11, wherein said first diameter is in the range of 2.0 to 20 mm.

15. The coil of claim 11, wherein said at least one winding comprises all windings of the main body windings, and said first diameter is a uniform diameter.

16. An assembly for use in occluding a vessel or a cavity within a vessel comprising:
    an elongated wire having a distal end; and
    a vasoocclusion coil mounted to said distal end of said wire, said coil having:
       a proximal end;
       a distal end;
       a coiled body formed of a multiplicity of windings having a proximal-most winding, a distal-most winding, and main body windings between said proximal-most and distal-most windings, said main body windings having a first diameter, and said proximal-most and distal-most winding a second diameter smaller than said first diameter, wherein said proximal end and said distal end are positioned radially inwardly of said proximal-most and distal-most windings, respectively, and said coil acts to occlude a vessel or a cavity when placed within the vessel or cavity; and
       fibers attached to said windings for facilitating embolization.

17. The assembly of claim 16, wherein said coil is a helical vasoocclusion coil.

18. The assembly of claim 16, wherein said first diameter is in the range of 0.2 mm to 30 mm.

19. The assembly of claim 16, wherein said first diameter is in the range of 2.0 to 20 mm.

20. The assembly of claim 16, wherein said at least one winding comprises all windings of the main body windings, and said first diameter is a uniform diameter.

* * * * *